United States Patent
Ruchti et al.

(10) Patent No.: US 6,990,364 B2
(45) Date of Patent: Jan. 24, 2006

(54) NONINVASIVE MEASUREMENT OF GLUCOSE THROUGH THE OPTICAL PROPERTIES OF TISSUE

(75) Inventors: Timothy L. Ruchti, Gilbert, AZ (US); Suresh N. Thennadil, New Castle upon Tyne (GB); Thomas B. Blank, Chandler, AZ (US); Alexander Lorenz, Chandler, AZ (US); Stephen L. Monfre, Gilbert, AZ (US)

(73) Assignee: Sensys Medical, Inc., Chandler, AZ (US)

(*) Notice: Subject to any disclaimer, the term of this patent is extended or adjusted under 35 U.S.C. 154(b) by 66 days.

(21) Appl. No.: 10/297,736

(22) PCT Filed: Jan. 25, 2002

(86) PCT No.: PCT/US02/02288

§ 371 (c)(1),
(2), (4) Date: Oct. 27, 2003

(87) PCT Pub. No.: WO02/065090

PCT Pub. Date: Aug. 22, 2002

(65) Prior Publication Data

US 2004/0068163 A1 Apr. 8, 2004

Related U.S. Application Data

(60) Provisional application No. 60/264,431, filed on Jan. 26, 2001.

(51) Int. Cl.
*A61B 5/00* (2006.01)

(52) U.S. Cl. .................. 600/310; 600/316; 600/473

(58) Field of Classification Search ........... 600/310, 600/322, 316, 473
See application file for complete search history.

(56) References Cited

U.S. PATENT DOCUMENTS

| | | | | | |
|---|---|---|---|---|---|
| 5,487,384 | A | * | 1/1996 | Lee | 600/316 |
| 5,551,422 | A | * | 9/1996 | Simonsen et al. | 600/322 |
| 5,729,333 | A | * | 3/1998 | Osten et al. | 356/39 |
| 5,743,262 | A | * | 4/1998 | Lepper et al. | 600/316 |
| 5,830,132 | A | * | 11/1998 | Robinson | 600/310 |
| 6,044,285 | A | | 3/2000 | Chaiken et al. | |
| 6,119,026 | A | | 9/2000 | McNulty et al. | |
| 6,212,424 | B1 | * | 4/2001 | Robinson | 600/475 |
| 6,615,061 | B1 | * | 9/2003 | Khalil et al. | 600/310 |

\* cited by examiner

*Primary Examiner*—Eric F. Winakur
(74) *Attorney, Agent, or Firm*—Glenn Patent Group; Michael A. Glenn

(57) ABSTRACT

Methods and apparatus for noninvasive determination of blood analytes, such as glucose, through NIR spectroscopy utilize optical properties of tissue as reflected in key spectroscopic features to improve measurement accuracy and precision. Physiological conditions such as changes in water distribution among tissue compartments lead to complex alterations in the measured absorbance spectrum of skin and reflect a modification in the effective pathlength of light, leading to a biased noninvasive glucose measurement. Changes in the optical properties of tissue are detected by identifying key features responsive to physiological variations. Conditions not conducive to noninvasive measurement of glucose are detected. Noninvasive glucose measurements that are biased by physiological changes in tissue are compensated. In an alternate embodiment, glucose is measured indirectly based on natural physiological response of tissue to glucose concentration. A spectroscopic device capable of such measurements is provided.

66 Claims, 6 Drawing Sheets

NONINVASIVE MEASUREMENT OF GLUCOSE THROUGH THE OPTICAL PROPERTIES OF TISSUE

This applications claims the benefit of Provisional Application No. 60/264,431, filed Jan. 26, 2001.

BACKGROUND OF THE INVENTION

1. Field of the Invention

The present invention relates generally to noninvasive tissue analyte determination. More particularly, the invention relates to methods and apparatus for characterizing physiological and chemical properties of an irradiated tissue sample by extracting spectral features reflecting optical properties of key tissue constituents. Subsequently, based on such spectral features, noninvasive glucose measurements that are biased by physiological changes in tissue are compensated. Alternatively, glucose is measured indirectly based on natural physiological response of tissue to shifts in glucose concentration.

2. Description of Related Art

Noninvasive Measurement of Glucose

Diabetes is a leading cause of death and disability worldwide and afflicts an estimated 16 million Americans. Complications of diabetes include heart and kidney disease, blindness, nerve damage and high blood pressure with the estimated total cost to United States economy alone exceeding $90 billion per year [*Diabetes Statistics*, Publication No. 98-3926, National Institutes of Health, Bethesda Md. (November 1997)]. Long-term clinical studies show that the onset of complications can be significantly reduced through proper control of blood glucose levels [The Diabetes Control and Complications Trial Research Group, *The effect of intensive treatment of diabetes on the development and progression of long-term complications in insulin-dependent diabetes mellitus*. N Eng J of Med. 329:977-86 (1993)]. A vital element of diabetes management is the self-monitoring of blood glucose levels by diabetics in the home environment. A significant disadvantage of current monitoring techniques is that they discourage regular use due to the inconvenient and painful nature of drawing blood through the skin prior to analysis. Therefore, new methods for self-monitoring of blood glucose levels are required to improve the prospects for more rigorous control of blood glucose in diabetic patients.

Numerous approaches have been explored for measuring blood glucose levels, ranging from invasive methods such as microdialysis to noninvasive technologies that rely on spectroscopy. Each method has associated advantages and disadvantages, but only a few have received approval from certifying agencies. To date, no noninvasive techniques for the self-monitoring of blood glucose have been certified.

One method, near-infrared spectroscopy involves the illumination of a spot on the body with near-infrared electromagnetic radiation (light in the wavelength range 750–2500 nm). The light is partially absorbed and scattered, according to its interaction with the constituents of the tissue prior to being reflected back to a detector. The detected light contains quantitative information that is based on the known interaction of the incident light with components of the body tissue including water, fat, protein and glucose.

Previously reported methods for the noninvasive measurement of glucose through near-infrared spectroscopy rely on the detection of the magnitude of light attenuation caused by the absorption signature of blood glucose as represented in the targeted tissue volume. The tissue volume is the portion of irradiated tissue from which light is reflected or transmitted to the spectrometer detection system. The signal due to the absorption of glucose is extracted from the spectral measurement through various methods of signal processing and one or more mathematical models. The models are developed through the process of calibration on the basis of an exemplary set of spectral measurements and associated reference blood glucose values (the calibration set) based on an analysis of capillary (fingertip) or venous blood.

Near-infrared spectroscopy has been demonstrated in specific studies to represent a feasible and promising approach to the noninvasive prediction of blood glucose levels. M. Robinson, R. Eaton, D. Haaland, G. Keep, E. Thomas, B. Stalled, P. Robinson, *Noninvasive glucose monitoring in diabetic patients: A preliminary evaluation*, Clin Chem, 38:1618–22 (1992) reports three different instrument configurations for measuring diffuse transmittance through the finger in the 600–1300 nm range. Meal tolerance tests were used to perturb the glucose levels of three subjects and calibration models were constructed specific to each subject on single days and tested through cross-validation. Absolute average prediction errors ranged from 19.8 to 37.8 mg/dl. H. Heise, R. Marbach, T. Koschinsky, F. Gries, *Noninvasive blood glucose sensors based on near-infrared spectroscopy*, Artif Org, 18:439–47 (1994); H. Heise, R. Marbach, *Effect of data pretreatment on the noninvasive blood glucose measurement by diffuse reflectance near-IR spectroscopy*, SPIE Proc, 2089:114–5 (1994); R. Marbach, T. Koschinsky, F. Gries, H. Heise, *Noninvasive glucose assay by near-infrared diffuse reflectance spectroscopy of the human inner lip*, Appl Spectrosc, 47:875–81 (1993) and R. Marbach, H. Heise, *Optical diffuse reflectance accessory for measurements of skin tissue by near-infrared spectroscopy*, Applied Optics 34(4): 610–21 (1995) present results through a diffuse reflectance measurement of the oral mucosa in the 1111–1835 nm range with an optimized diffuse reflectance accessory. In vivo experiments were conducted on single diabetics using glucose tolerance tests and on a population of 133 different subjects. The best standard error of prediction reported was 43 mg/dl and was obtained from a two-day single person oral glucose tolerance test that was evaluated through cross-validation.

K. Jagemann, C. Fischbacker, K. Danzer, U. Muller, B. Mertes, *Application of near-infrared spectroscopy for noninvasive determination of blood/tissue glucose using neural network*, Z Phys Chem, 191S:179–190 (1995); C. Fischbacker, K. Jagemann, K. Danzer, U. Muller, L. Papenkrodt, J. Schuler, *Enhancing calibration models for noninvasive near-infrared spectroscopic blood glucose determinations*, Fresenius J Anal Chem 359:78–82 (1997); K. Danzer, C. Fischbacker, K. Jagemann, K. Reichelt, *Near-infrared diffuse reflection spectroscopy for noninvasive blood-glucose monitoring*, LEOS Newsletter 12(2):9–11 (1998); and U. Muller, B. Mertes, C. Fischbacker, K. Jagemann, K. Danzer, *Noninvasive blood glucose monitoring by means of new infrared spectroscopic methods for improving the reliability of the calibration models*, Int J Artif Organs, 20:285–290 (1997) recorded spectra in diffuse reflectance over the 800–1350 nm range on the middle finger of the right hand with a fiber-optic probe. Each experiment involved a diabetic subject and was conducted over a single day with perturbation of blood glucose levels through carbohydrate loading. Results, using both partial least squares regression and radial basis function neural networks were evaluated on single subjects over single days through cross-validation. Danzer, et al., supra, report an average root mean square prediction error of 36 mg/dl through cross-validation over 31 glucose profiles.

J. Burmeister, M. Arnold, G. Small, *Human noninvasive measurement of glucose using near infrared spectroscopy* [abstract], Pittcon, New Orleans, La. (1998) collected absorbance spectra through a transmission measurement of the tongue in the 1429–2000 nm range. A study of five diabetic subjects was conducted over a 39-day period with five samples taken per day. Every fifth sample was used for an independent test set and the standard error of prediction for all subjects was greater than 54 mg/dl.

In T. Blank, T. Ruchti, S. Malin, S. Monfre, *The use of near-infrared diffuse reflectance for the noninvasive prediction of blood glucose*, IEEE Lasers and Electro-Optics Society Newsletter, 13:5 (October 1999), the reported studies demonstrate noninvasive measurement of blood glucose during modified oral glucose tolerance tests over a short time period. The calibration was customized for the individual and tested over a relatively short time period.

In all of these studies, limitations were cited that would affect the acceptance of such a method as a commercial product. These limitations included sensitivity, sampling problems, time lag, calibration bias, long-term reproducibility and instrument noise.

Fundamentally, however, accurate noninvasive estimation of blood glucose is presently limited by the available near-infrared technology, the trace concentration of glucose relative to other constituents and the dynamic nature of the skin and living tissue of the patient (for example, see O. Khalil, *Spectroscopic and clinical aspects of noninvasive glucose measurements*, Clin Chem, 45:165–77 (1999)). As reported by S. Malin, T. Ruchti, *An Intelligent System for Noninvasive Blood Analyte Prediction*, U.S. Pat. No. 6,280,381 (Aug. 28, 2001), the entirety of which is hereby incorporated by reference, chemical, structural and physiological variations occur that produce dramatic and nonlinear changes in the optical properties of the tissue sample [see R. Anderson, J. Parrish, *The optics of human skin*, Journal of Investigative Dermatology, 7:1, pp.13–19 (1981), W. Cheong, S. Prahl, A. Welch, *A review of the optical properties of biological tissues*, IEEE Journal of Quantum Electronics, 26:12, pp.2166–2185, (December 1990), D. Benaron, D. Ho, *Imaging (NIRI) and quantitation (NIRS) in tissue using time-resolved spectrophotometry: the impact of statically and dynamically variable optical path lengths*, SPIE, 1888, pp.10–21 (1993), J. Conway, K. Norris, C. Bodwell, *A new approach for the estimation of body composition: infrared interactance*, The American Journal of Clinical Nutrition, 40, pp.1123–1140 (December 1984), S. Homma, T. Fukunaga, A. Kagaya, *Influence of adipose tissue thickness in near infrared spectroscopic signals in the measurement of human muscle*, Journal of Biomedical Optics, 1:4, pp.418–424 (October 1996), A. Profio, *Light transport in tissue*, Applied Optics, 28:12), pp. 2216–2222, (June 1989), M. Van Gemert, S. Jacques, H. Sterenborg, W. Star, *Skin optics*, IEEE Transactions on Biomedical Engineering, 36:12, pp.1146–1154 (December 1989), and B. Wilson, S. Jacques, *Optical reflectance and transmittance of tissues: principles and applications*, IEEE Journal of Quantum Electronics, 26:12, pp. 2186–2199].

The measurement is further complicated by the heterogeneity of the sample, the multi-layered structure of the skin and the rapid variation related to hydration levels, changes in the volume fraction of blood in the tissue, hormonal stimulation, temperature fluctuations and blood analyte levels. This can be further considered through a discussion of the scattering properties of skin.

Tissue Scattering Properties

Skin Structure

The structure and composition of skin varies widely among individuals as well as between different sites and over time on the same individual. Skin consists of a superficial layer known as the stratum corneum, a stratified cellular epidermis, and an underlying dermis of connective tissue. Below the dermis is the subcutaneous fatty layer or adipose tissue. The epidermis, with a thickness of 10–150 $\mu$m, together with the stratum corneum provides a barrier to infection and loss of moisture, while the dermis is the thick inner layer that provides mechanical strength and elasticity [F. Ebling, *The Normal Skin, Textbook of Dermatology*, $2^{nd}$ ed.; A. Rook; D. Wilkinson, F. Ebling, Eds.; Blackwell Scientific, Oxford, pp 4–24 (1972)]. In humans, the thickness of the dermis ranges from 0.5 mm over the eyelid to 4 mm on the back and averages approximately 1.2 mm over most of the body [S. Wilson, V. Spence, Phys. Med. Biol., 33:894–897 (1988)].

In the dermis, water accounts for approximately 70% percent of the volume. The next most abundant constituent is collagen, a fibrous protein comprising 70–75% of the dry weight of the dermis. Elastin fibers, also a protein, are plentiful though they constitute only a small proportion of the bulk. In addition, the dermis contains a wide variety of structures (e.g., sweat glands, hair follicles and blood vessels) and other cellular constituents [see F. Ebling, supra]. Conversely, the subcutaneous layer (adipose tissue) is by volume approximately 10% water and consists primarily of cells rich in triglycerides (fat). The concentration of glucose varies in each layer according to the water content, the relative sizes of the fluid compartments, the distribution of capillaries and the perfusion of blood. Due to the high concentration of fat, the average concentration of glucose in subcutaneous tissue is significantly lower than that of the dermis.

Optical Properties of Skin

When near-infrared light is delivered to the skin, a percentage of it is reflected, while the remainder penetrates into the skin. The proportion of reflected light, or specular reflectance is typically between 4–7% of the delivered light over the entire spectrum from 250–3000 nm (for a perpendicular angle of incidence) [J. Parrish, R. Anderson, F. Urbach, D. Pitts, *UV-A: Biologic Effects of Ultraviolet Radiation with Emphasis on Human Responses to Longwave Ultraviolet*, New York, Plenum Press (1978)]. The 93–96% of the incident light that enters the skin is attenuated due to absorption and scattering within the many layers of the skin. These two processes, combined with orientation of the sensors of the spectrometer instrument, determine the tissue volume irradiated by the source and "sampled" through the collection of diffusely reflected light.

Diffuse reflectance or remittance is defined as that fraction of incident optical radiation that is returned from a turbid sample. Alternately, diffuse transmittance is the fraction of incident optical radiation that is transmitted through a turbid sample. Absorption by the various skin constituents mentioned above accounts for the spectral extinction of the light within each layer. Scattering is the only process by which the beam may be returned to contribute to the diffuse reflectance of the skin. Scattering also has a strong influence on the light that is diffusely transmitted through a portion of the skin.

The scattering in tissues is due to discontinuities in the refractive index on the microscopic level, such as the aqueous-lipid membrane interfaces between each tissue compartment or the collagen fibrils within the extracellular matrix [B. Wilson, S. Jacques, *Optical reflectance and*

*transmittance of tissues: principles and applications*, IEEE Journal of Quantum Electronics, 26:12 (December 1990)]. The spatial distribution and intensity of scattered light depends upon the size and shape of the particles relative to the wavelength, and upon the difference in refractive index between the medium and the constituent particles. The scattering of the dermis is dominated by the scattering from collagen fiber bundles in the 2.8 µm diameter range occupying twenty-one percent of the dermal volume, and the refractive index mismatch is 1.38/1.35 [S. Jacques, *Origins of tissue optical properties in the UVA, Visible and NIR Regions*, Optical Society of America, Topical Meeting, Orlando Fla. (Mar. 18–22, 1996)]. The spectral characteristics of diffuse remittance from tissue result from a complex interplay of the intrinsic absorption and scattering properties of the tissue, the distribution of the heterogeneous scattering components and the geometry of the point(s) of irradiation relative to the point(s) of light detection.

The absorption of light in tissue is primarily due to three fundamental constituents: water, protein and fat. As the main constituent, water dominates the near-infrared absorbance above 1100 nm and is observed through pronounced absorbance bands (for example, see FIG. 3). Protein in its various forms, and in particular collagen, is a strong absorber of light that irradiates the dermis. Near-infrared light that penetrates to subcutaneous tissue is absorbed primarily by fat. In the absence of scattering, the absorbance of near-infrared light due to a particular analyte, A, can be approximated by Beers Law at each wavelength by $$A = \epsilon c l \quad (1)$$

where $\epsilon$ is the analyte specific absorption coefficient, c is the concentration and/is the pathlength. The overall absorbance at a particular wavelength is the sum of the individual absorbances of each particular analyte given by Beer's Law. The concentration of a particular analyte, such as glucose, can be determined through a multivariate analysis of the absorbance over a multiplicity of wavelengths because $\epsilon$ is unique for each analyte. However, in tissue compartments expected to contain glucose, the concentration of glucose is at least three orders of magnitude less than that of water. Consequently, the signal targeted for detection by reported approaches to near-infrared measurement of glucose (the absorbance due to glucose in the tissue) is expected to be at most three orders of magnitude less than other interfering tissue constituents. Therefore, the near-infrared measurement of glucose requires a high level of sensitivity over a broad wavelength range, and the application of methods of multivariate analysis.

However, the diverse scattering characteristics of the skin (e.g., multiple layers and heterogeneity) cause the light returning from an irradiated sample to vary in a highly nonlinear manner with respect to tissue analytes, in particular, glucose. Simple linear models, such as the Beer's Law have been reported to be invalid for the dermis [R. Anderson, J. Parrish, *The optics of human skin*, Journal of Investigative Dermatology, 77:1, pp. 13–19 (1981).]. Such nonlinear variation is a recognized problem and several reports have disclosed unique methods for compensating for the nonlinearity of the measurement while providing the necessary sensitivity [see S. Malin, et al., supra; E. Thomas, R. Rowe, *Methods and Apparatus for Tailoring Spectroscopic Calibration Models*, U.S. Pat. No. 6,157,041 (Dec. 5, 2000).].

Dynamic Properties of the Skin

While knowledge of and utilization of the optical properties of the skin, high instrument sensitivity and compensation for inherent nonlinearities are all vital for the application of near-infrared spectroscopy to noninvasive blood analyte measurement, an understanding of biological and chemical mechanisms that lead to time dependent changes in the optical properties of skin tissue is equally important and, yet, largely ignored. At a given measurement site, skin tissue is often assumed to be static except for changes in the target analyte and other absorbing species. However, variations in the physiological state of tissue profoundly affect the optical properties of tissue layers and compartments over a relatively short period of time. Such variations are often dominated by fluid compartment equalization through water shifts and are related to hydration levels and changes in blood analyte levels.

Total body water accounts for over 60% of the weight of the average person and is distributed between two major compartments: the extracellular fluid (one-third of total body water) and the intracellular fluid (two-thirds of total body water) [see A. Guyton, J. Hall, *Textbook of Medical of Physiology*, $9^{th}$ ed., Philadelphia, W. B. Saunders Company (1996)]. The extracellular fluid in turn is divided into the interstitial fluid (extravascular) and the blood plasma (intravascular). Water permeable lipid membranes separate the compartments and water is transferred rapidly between them through the process of diffusion, in order to equalize the concentrations of water and other analytes across the membrane. The net water flux from one compartment to another constitutes the process of osmosis and the amount of pressure required to prevent osmosis is termed the osmotic pressure. Under static physiological conditions the fluid compartments are at equilibrium. However, during a net fluid gain or loss as a result of water intake or loss, all compartments gain or lose water proportionally and maintain a constant relative volume.

The primary mechanism for distributing substances contained in blood serum that are needed by the tissues, such as water and glucose, is through the process of diffusion. The invention recognizes that Fick's law of diffusion drives the short-term intra-/extra vascular fluid compartment balance. The movement of water and other analytes from intravascular to extravascular compartments occurs rapidly as tremendous numbers of molecules of water and other constituents, in constant thermal motion, diffuse back and forth through the capillary wall. On average, the rate at which water molecules diffuse through the capillary membrane is about eighty times greater than the rate at which the plasma itself flows linearly along the capillary. In the Fick's Law expression, the actual diffusion flux, $I_{OA}$, is proportional to the concentration gradient, dc/dx between the two compartments and the diffusivity of the molecule, $D_A$ according to the equation $$I_{OA} = -D_A \frac{-dc}{dx}. \quad (2)$$

Short-term increases (or decreases) in blood glucose concentrations lead to an increase (or decrease) in blood osmolality (number of molecules per unit mass of water). Fluid is rapidly re-distributed accordingly and results in a change in the water concentration of each body compartment. For example, the osmotic effect of hyperglycemia is a movement of extravascular water to the intravascular space. Conversely, a decrease in blood glucose concentration leads to a movement of water to extravascular space from the intravascular compartment.

Because the cell membrane is relatively impermeable to most solutes but highly permeable to water, whenever there is a higher concentration of a solute on one side of the cell membrane, water diffuses across the membrane toward the region of higher solute concentration. Large osmotic pressures can develop across the cell membrane with relatively small changes in the concentration of solutes in the extracellular fluid. As a result, relatively small changes in concentration of impermeable solutes in the extracellular fluid, such as glucose, can cause tremendous changes in cell volume.

Long-term fluid compartment balances are influenced by fluid intake, exercise, diet, drug therapy and other physiological factors. The ancillary calibration of glucose to fluid compartment shifts is possible over short-term periods. The calibration of glucose to fluid shifts over longer periods of time requires a bias correction of the analytical signal and the associated blood glucose to compensate for the sources of long-term fluid compartment shifts. It is noted that Fick's Law (equation 2) relates the flux in water concentration to the change in glucose concentration. Thus, this measurement based on first principles only permits the determination of the relative movement of glucose. Bias correction of both the spectroscopic water signal and the associated glucose concentration are required because the initial water concentration is not strictly a function of the associated glucose concentration. Accordingly, without more, it is only feasible to predict relative movement of glucose. Generating an absolute glucose value would require using a paired glucose/water measurement to adjust the time dependent bias in the ancillary fluid shift signal.

The Problem

Re-distribution of water between various tissue compartments alters the optical properties of the tissue through changes in the water concentration, the concentration of other analytes, the refractive indices of various layers, the thickness of tissue layers and the size and distribution of scattering centers. Therefore, the optical properties of the tissue sample are modified in a highly nonlinear and profound manner. In addition, the actual tissue volume sampled (and the effective or average pathlength of light) is varied. Consequently, the spectral measurement varies in a complex manner that is incompatible with current modes of near-infrared detection of glucose. For example, changes in blood glucose concentration will result in water compartment shifts to compensate for the increase or decrease in intravascular osmolality. A change in the distribution of water will lead to a rapid change in the optical properties of the tissue that is correlated to a change in the absorption of glucose.

Several methods are reported to compensate in some part for the dynamic variation of the tissue. For example, several reported methods of noninvasive glucose measurement develop calibration models that are specific to an individual over a short period of time [see Robinson, et al., supra; Burmeister et al., supra; Blank et al., supra; K. Hazen, *Glucose determination in biological matrices using near-infrared spectroscopy*, Doctoral Dissertation, University of Iowa (August, 1995); and J. Burmeister, *In vitro model for human noninvasive blood glucose measurements*, Doctoral Dissertation, University of Iowa (December 1997]. This approach avoids modeling the differences between patients and therefore cannot be generalized to more individuals. However, the calibration models have not been tested over long time periods and no means of compensating for variation related to the dynamic water shifts of fluid compartments is reported.

Malin and Ruchti, supra report a method for compensating for variation related to the structure and state of the tissue through an intelligent pattern recognition system capable of determining calibration models that are most appropriate for the patient at the time of measurement. The calibration models are developed from the spectral absorbance of a representative population of patients that have been segregated into groups. The groups or classes are defined on the basis of structural and state similarity such that the variation within a class is small compared to the variation between classes. Classification occurs through extracted features of the tissue absorbance spectrum related to the current patient state and structure. However, the described invention does not use features for directly compensating for physiological changes in the tissue. Further, the direct use of features representing the physiological state of the subject (or subject's measurement site) for noninvasive measurement of glucose was not described.

E. Thomas, R. Rowe, *Methods and Apparatus for Tailoring Spectroscopic Calibration Models*, U.S. Pat. No. 6,157,041 (Dec. 5, 2000) identifies a method for reducing intra-subject variation through the process of mean-centering both the direct and indirect measurements. However, this does not address the key problem related to short-term physiological and chemical changes related to the dynamic nature of the tissue.

No reported method provides a method and apparatus for detecting features that reflect changes in the optical properties of tissue related to physiological properties of the tissue such as the shifting of water between fluid compartments. Second, no reported method utilizes features that reflect the dynamic nature of the tissue to detect conditions unsuitable for near-infrared measurement of blood glucose. Third, no method exists to use these features to compensate glucose measurements for bias caused by physiological changes. Finally, no reported method utilizes fluid compartment shifts as reflected in spectral features related to the optical properties of tissue to indirectly measure glucose. As a result, noninvasive measurement of glucose is limited by the dynamic nature of tissue related to the tissue's physiological response to various conditions and the re-distribution of water among tissue fluid compartments.

In view of the problems left unsolved by the prior art, there exists a need for a method and apparatus to first detect changes in the optical properties of the tissue due to the changing physiology of the subject, specifically changes related to water shifts between tissue compartments. Second, use of these features to determine conditions unsuitable for glucose measurement through near-infrared spectroscopy would be a useful advancement. Finally, it would be a significant advancement to determine a means for either using the features to compensate for the changing optical properties of the tissue or alternately, utilizing the features to measure glucose.

SUMMARY OF THE INVENTION

Changes in the distribution of water among tissue compartments and other physiological conditions lead to complex alterations in the measured absorbance spectrum of skin and reflect a modification in the effective pathlength of light. These dynamic changes lead to a biased noninvasive glucose measurement and have limited the state of the technology. This disclosure provides a method and apparatus for utilizing the optical properties of tissues as reflected in key spectroscopic features to improve the accuracy and precision of the noninvasive measurement of glucose through near-infrared spectroscopy. Specifically, a method is provided for detecting changes in the optical properties of tissue through the identification of key features that are responsive to and reflect physiological variations. Secondly, a process is given for detecting conditions that are not conducive to noninvasive measurement of glucose. Third, a means is provided for compensating noninvasive glucose measurements that are biased by physiological changes in the tissue. Fourth, a method is disclosed for measuring glucose indirectly on the basis of the natural physiological response of the tissue to the concentration of glucose. Finally, the apparatus required to make such a measurement is detailed.

DETAILED DESCRIPTION

Figure 1:
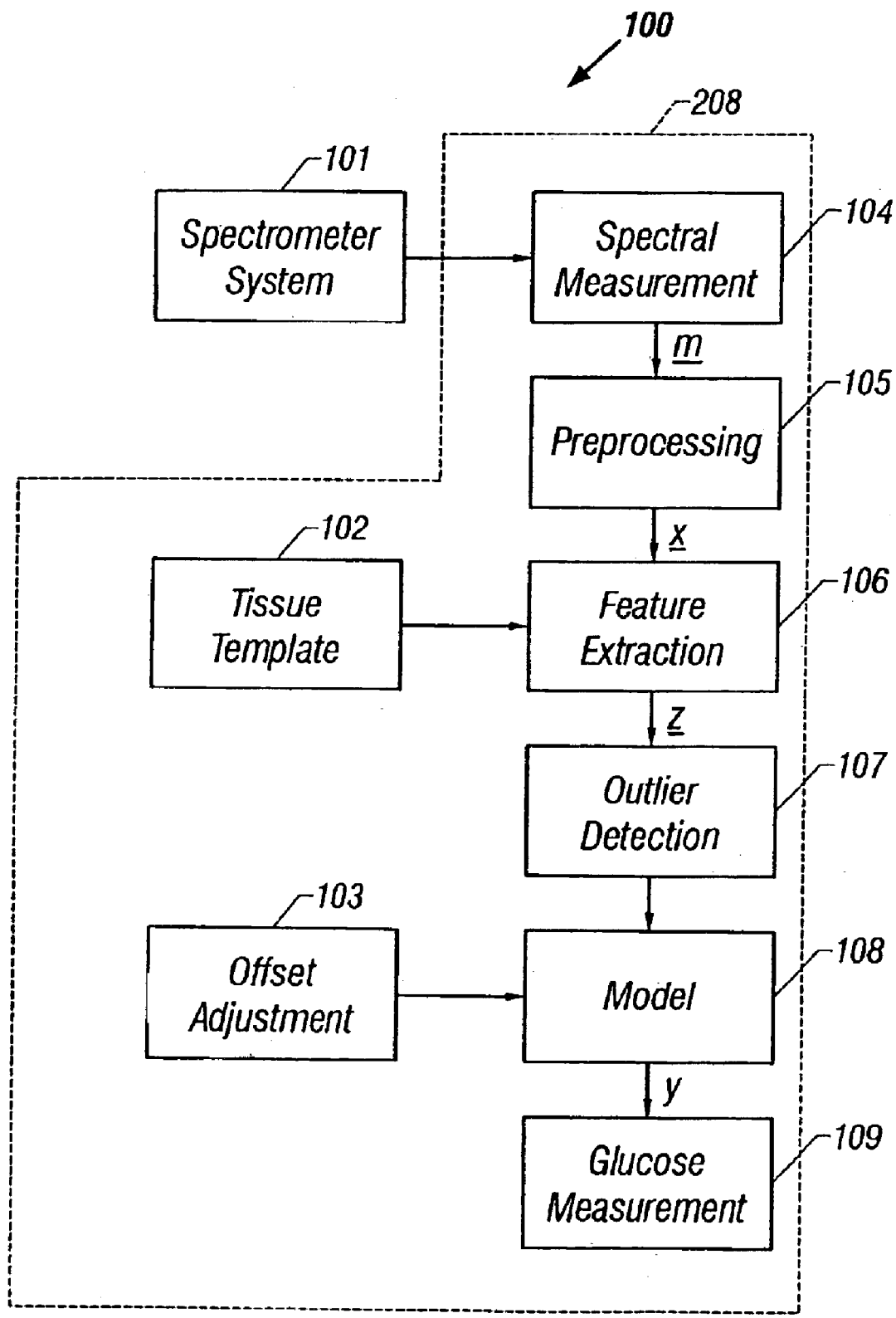
FIG. 1 provides a block diagram of a system for measuring glucose noninvasively through near-infrared spectroscopy according to the invention.
Figure 2:
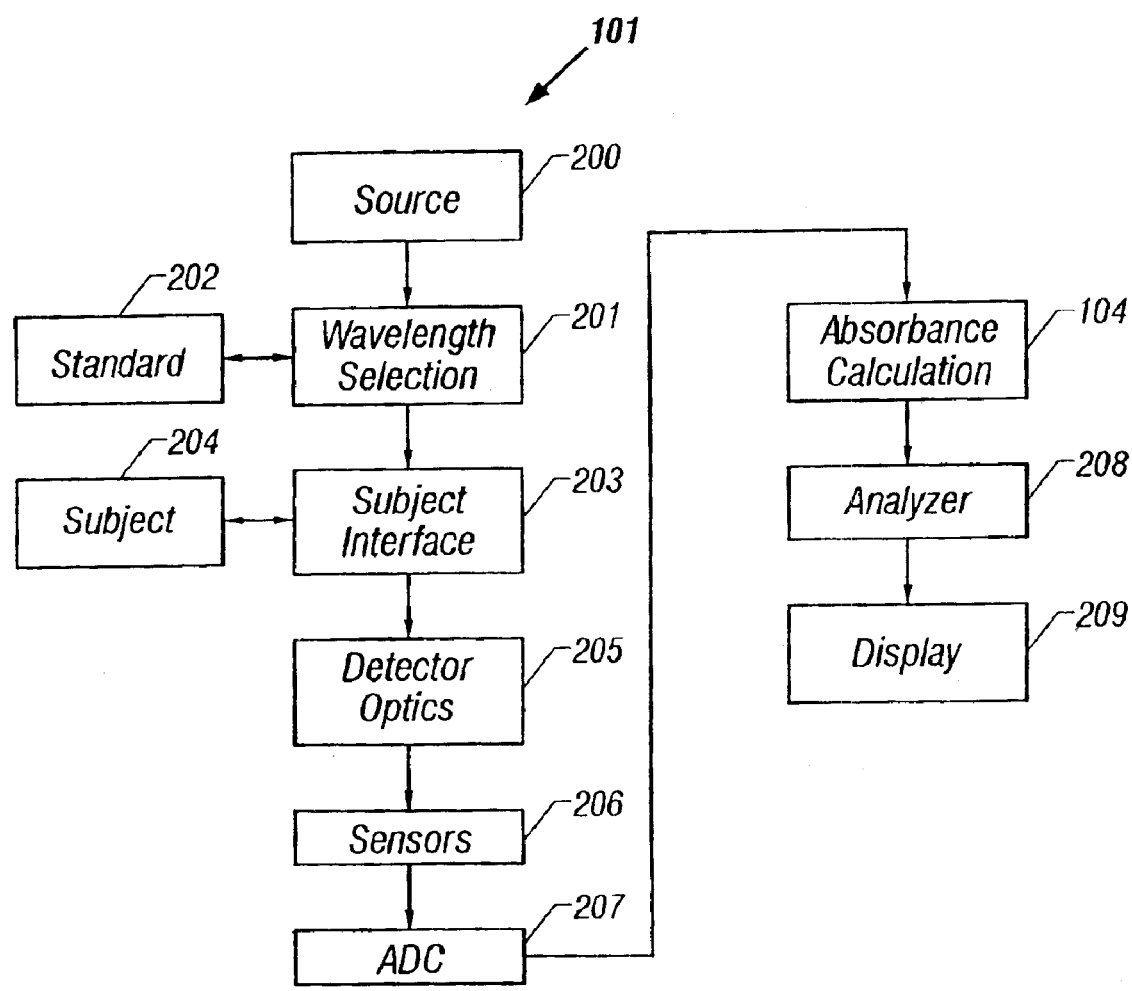
FIG. 2 provides a block diagram of a spectrometer from the system of FIG. 1 according to the invention.

A major difficulty in noninvasively measuring glucose through near-infrared spectroscopy arises from the fact that glucose is present in very small amounts (2–20 mM). Calibrating a sensor to this small glucose signal requires extraction of the signal from a massive background due to variations in tissue characteristics and hydration. These background variations result in changes in the optical properties of the sampled tissue leading to confounding effects due to the resulting pathlength changes causing large uncertainties in the extracted signal. Long-term variations (over a few days) in tissue characteristics are especially bothersome since their effects could be large enough to swamp the small glucose signal. While the glucose signal is small, changes in blood glucose triggers physiological responses that are large. A major physiological response that can be detected spectrally is the fluid shift that occurs due to changes in blood glucose, which causes water to move in and out of the vascular and cellular compartments. This redistribution of water causes changes in the scattering and absorption properties of skin leading to significant changes in the observed spectra of skin. This change in spectra due to changes in fluid distribution as a response to changes in blood glucose has proven extremely useful for building robust calibration models for glucose measurement.

More specifically, changes in blood glucose leads to changes in the distribution and content of water in skin tissue. This variation causes a change in the refractive index (and thus the scattering coefficient) and a change in the absorption coefficient of tissue. As a result, the depth to which light penetrates the tissue is changed. In the case of a diffuse reflectance measurement, the changes in the absorption and scattering properties affect the amount of light from a certain depth in the tissue that reaches the detector. For example, changes in the water content in the dermis will dictate the amount of light reaching the detector that has probed the subcutaneous tissue and thereby changes the total amount of light that is absorbed by fat. In other words, changes in the fluid distribution will change the magnitude of the fat absorbance signal detected. The invention described herein below is based upon this discovery.

In recognition of the above discovery, the invention provides a method for detecting changes in the optical properties of tissue related to physiological changes, such as the water distribution among various compartments, for determining conditions that are not conducive to noninvasive measurement of glucose through near-infrared spectroscopy, and for:

correcting the glucose measurement on the basis of detected changes in tissue optical properties; or measuring glucose indirectly on the basis of features reflecting the detected optical properties.

An apparatus for detecting and correcting fluid compartment changes and indirectly measuring glucose includes, but is not limited to:

a spectrometer system;

a patient interface module; and an analyzer.

The spectrometer system detects near-infrared light within a specified range that is diffusely transmitted or reflected from the targeted tissue, and the analyzer measures glucose through data processing operations and the application of a model. Fundamental to the system is the patient interface module, which precisely couples the apparatus to the tissue measurement site physically and optically, with minimal disturbance. In addition, a means, such as an optical coupling medium, is provided for preparing the sample site for spectroscopic measurement prior to contact with the device for the purpose of reducing specular reflectance and the effects of skin temperature and skin hydration changes.

An overview of the system is shown in FIG. 1 and generally consists of two elements, a spectrometer 101 or instrument and an analyzer 208 embodying the process for obtaining the glucose measurement. The spectrometer measures the near-infrared spectrum of a subject's tissue. The analyzer processes the spectral measurement, extracts features relevant to outlier detection and glucose measurement and applies a model to the processed spectral measurement and/or the extracted features to obtain a glucose measurement. A detailed description of the spectrometer by system and the components of the analyzer follow.

Spectrometer System

The spectroscopic measurement system 101 consists of a source of near-infrared radiation 200, a wavelength selection system 201, an interface to the patient, a means for directing the near-infrared radiation to the skin 203 and a means for directing radiation reflected or transmitted from the skin 205, a means for detecting near-infrared radiation that is reflected or transmitted from the skin 206, a means for analyzing the detected near-infrared radiation 208 and a means for displaying the measured analyte, property or constituent 209.

In an alternate arrangement, the wavelength selection 201 can occur between the subject interface 203 and the detector optics 205.

The source 200 radiates near-infrared energy in the wavelength range 700–2500 nm and may consist of, for example, an array of LED's or a halogen lamp. One or more bandpass filters are (optionally) required to minimize the effect of wavelengths from outside of the spectral range of interest, but which are still emitted by the source of near-infrared energy. For example, halogen lamps, while having peak energy at approximately 1600 nm, still give off electromagnetic radiation above 2500 nm. This has detrimental effects on the detection of glucose since wavelengths above 2500 nm have deleterious effects at the measurement site due to heating of the tissue and its respective components.

The method of wavelength separation 201 before and or after illumination of the skin can be performed through the use of a dispersive element (e.g., a plane or concave, ruled or holographic grating), an interferometer, or successive illumination of the elements of an LED array without an additional dispersive element. Due to changes in performance of these wavelength separation methods caused by changes in the environment, it is necessary to correct for these changes by scanning a reference wavelength standard 202, for example a polystyrene standard, either immediately before or after the interrogation of the tissue. In interferometer-based systems, this is done simultaneously with the interrogation of the tissue.

The sensing element(s) 206 are detectors that are responsive to the targeted wavelengths and may constitute either an array or a single element. In the case of linear diode arrays (or photodiode arrays), when two or more different detector materials are required to cover the wavelength region of interest, it is preferable that the material junction(s) occurs at a wavelength not required for the measurement. For example, in the case of InGaAs and extended InGaAs detectors, the junction typically occurs at 1750 nm for the purpose of reducing the cost of the array due to the high cost of extended InGaAs. However, this wavelength region occurs in the middle of the absorptions associated with fat, protein and glucose; thus, it is much preferable for the junction to occur at approximately 1480 nm±20 nm. In addition, it is preferable that the electronics used to sense the individual elements of the array have their junction occurring at the same wavelength.

The tissue sample interface includes a subject 204 interface module 203 by which near-infrared radiation is directed to and from 205 the tissue, either directly or through a light pipe, fiber optics, a lens system or a light directing mirror system. The area of the tissue surface to be irradiated and the area from which the returning near-infrared radiation is detected fare different, being separated by a defined distance and selected in order to target a tissue volume optimal to measurement of the property of interest. The specularly reflected radiation from the irradiated site is of such a magnitude that it would greatly interfere with detection of the returned radiation. Thus, in offsetting the detection site from the irradiation site by a predetermined amount, it is possible to sample a volume of tissue that is a subset of the manifold of tissue that has affected the light that is being detected, while avoiding interference from specularly reflected light. In the case of a larger, tabletop or desktop instrument, the patient interface module further includes an elbow rest, a wrist rest, and a guide to assist in interfacing the illumination mechanism of choice and the tissue of interest. In the case of a smaller handheld unit, the patient interface module includes a guide or positioning mechanism to assist in interfacing the tissue of interest. Generally, as described above, an optical coupling fluid is placed between the illumination mechanism and the tissue of interest to minimize specular reflectance from the surface of the skin. Portions of the aforementioned patient interface module are described in U.S. patent application Ser. No. 09/563,782 and PCT Application No. US01/29232, the contents of both of which are hereby incorporated by reference in their entirety.

The collected near-infrared radiation is converted to a voltage and sampled through an analog-to-digital 207 converter for analysis on a microprocessor-based system 208 and the result of such analysis displayed 209.

The sample site, the surface or point on the subject the measurement probe comes into contact with, includes the specific tissue irradiated by the spectrometer system. The ideal qualities of the sample site include homogeneity, immutability and accessibility to the target analyte. While several measurement sites can be used, including the abdomen, thigh, hand (palm or back of the hand), ear lobe or finger, in the preferred embodiment, the volar part of the forearm is used. In addition, while the measurement can be made in either diffuse reflectance or diffuse transmittance mode, the preferred method is diffuse reflectance. The scanning of the tissue can be done continuously, in the case of an area not subject to pulsation effects, or the scanning can be done intermittently between pulses.

Spectral Measurement

Figure 3:
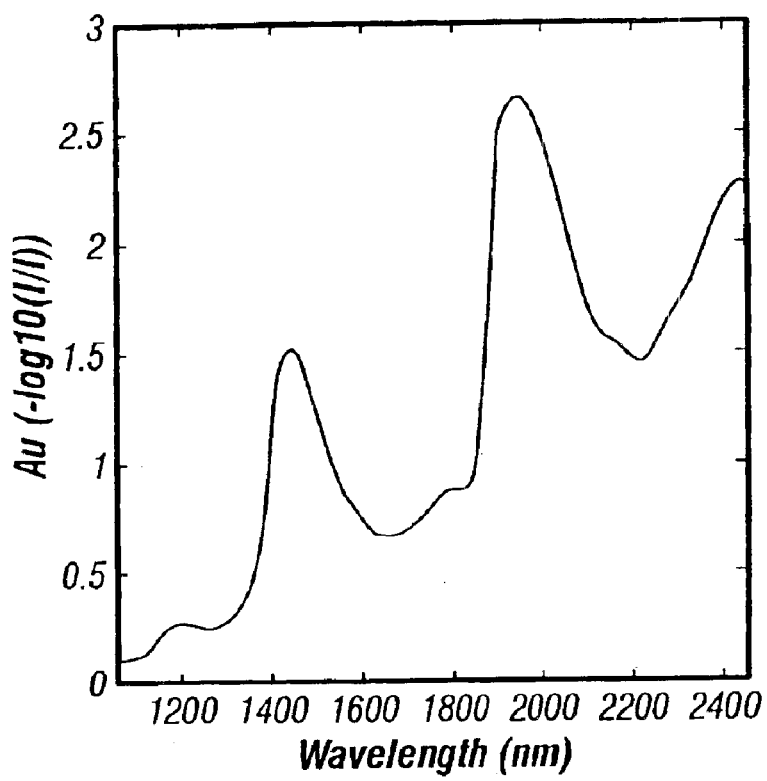
FIG. 3 shows a typical absorbance spectrum measurement from the forearm of a human subject.

The spectrometer system provides a spectral measurement 104 or "spectrum" to the analyzer 208 for determination or measurement of the concentration of glucose. The spectrum is denoted by the vector $m \in \Re^{1 \times N}$ of absorbance values pertaining to a set of N wavelengths $\lambda \in \Re^N$ that span the near-infrared portion (700–2500 nm) of the spectrum. In the preferred embodiment, the measurement process and absorbance calculation is as follows: the measured intensity of light from the tissue, $I \in \Re^{1 \times N}$, and the light intensity measured from a non-absorbing reference material, $I_o \in \Re^{1 \times N}$, are used to determine m according to $$m = -\log_{10} \frac{I}{I_o} \qquad (3)$$

where m is the reflectance spectrum of the skin and is analogous to an absorbance spectrum containing quantitative information that is based on the known interaction of the incident light with components of the body tissue. A plot of m versus λ is shown in FIG. 3, and consists of absorption bands primarily due to water, fat and protein. More particularly, however, the measurement can consist of a specific set of wavelengths in the near infrared region that have been optimized for the extraction of features and for the measurement requirements. For example, the measurement of glucose is optimally performed in the wavelength range 1100–1935 nm, or a selected subset thereof.

Alternatively, the spectral measurement can be determined according to $$m = -\log_{10} \frac{I}{I_r} \qquad (4)$$

where $I_r \in \Re^{1 \times N}$ is a representation of the measured tissue intensity at some point in time prior to collection of I and can be determined from a single tissue intensity spectrum or from the mean or a robust estimate of the mean (e.g., the trimmed mean) of several tissue intensity spectra. In another embodiment, the measurement m, can be defined as the measured intensity, I. Finally, m may consist of either a single spectrum collected with an instrument or a combination of several (optimally) selected spectra collected over a defined measurement period and averaged. Methods for selecting the spectra, used to produce the lowest noise measurement, include similarity or distance measures (i.e., select the most similar) and clustering operations.

Preprocessing and Feature Extraction

Feature extraction 106 is any mathematical transformation that enhances a quality or aspect of the sample measurement for interpretation [R. Duda, P. Hart, *Pattern Classification and Scene Analysis*, John Wiley and Sons, New York (1973)]. The general purpose of feature extraction is to concisely represent or enhance the chemical concentration, structural properties and physiological state of the tissue measurement site. In the invention, a set of features is developed that represents or reflects the optical properties of the tissue based on:

identification of distinct absorption bands that change in various ways with respect to changes in pathlength; and the scattering and absorption properties (or coefficients) of the measurement site.

Subsequently, the features are then applied either to identify conditions unsuitable for glucose measurement or to perform an actual measurement of glucose. For example, a resolved estimate of the magnitude of the fat band absorbance can be used to infer specific information about the dermis. Although fat is absent from the dermis, near infrared radiation must propagate through the dermis to penetrate into the adipose tissue beneath. Thus, physiological changes, and the corresponding changes in the optical properties of the dermis, influence the magnitude of the fat band absorbance.

Thus, as water concentration in the dermis increases, the magnitude of the fat band naturally decreases and vice versa.

Several types of features are determined and used in the invention for:

outlier detection 107;

compensation for changes in the optical properties of tissue 102; and glucose measurement 109.

Given the spectral measurement, m, or a spectral measurement pre-processed 105 by means of a filtering operation, first or second derivative calculation [A. Savitzky, M. Golay, *Smoothing and Differentiation of Data by Simplified Least Squares Procedures*, Anal. Chem., 36: 8, pp. 1627–1639 (1964)] or scatter correction:

"simple" features are the values of the spectral measurement or the processed spectral measurement at the critical points (the points at which the slope is zero);

additional (derived) features are determined from the base features through mathematical transformation such as addition, subtraction, division and multiplication; and abstract features are derived through linear and nonlinear transformations of the pre-processed spectrum.

While simple and derived features generally have a physical interpretation, such as the magnitude of the fat absorbance, the set of abstract features do not necessarily have a specific interpretation related to the physical system. For example, the scores of a principal component analysis are used as features although their physical interpretation is not always known. The utility of the principal component analysis is related to the nature of the tissue absorbance spectrum. The most significant variation in the tissue spectral absorbance is not caused by the absorption of glucose but is related to the state, structure and composition of the measurement site. This variation is modeled by the primary principal components. Therefore, the leading principal components tend to represent variation related to the structural properties and physiological state of the tissue measurement site and consequently reflect the optical properties of tissue.

Figure 4:
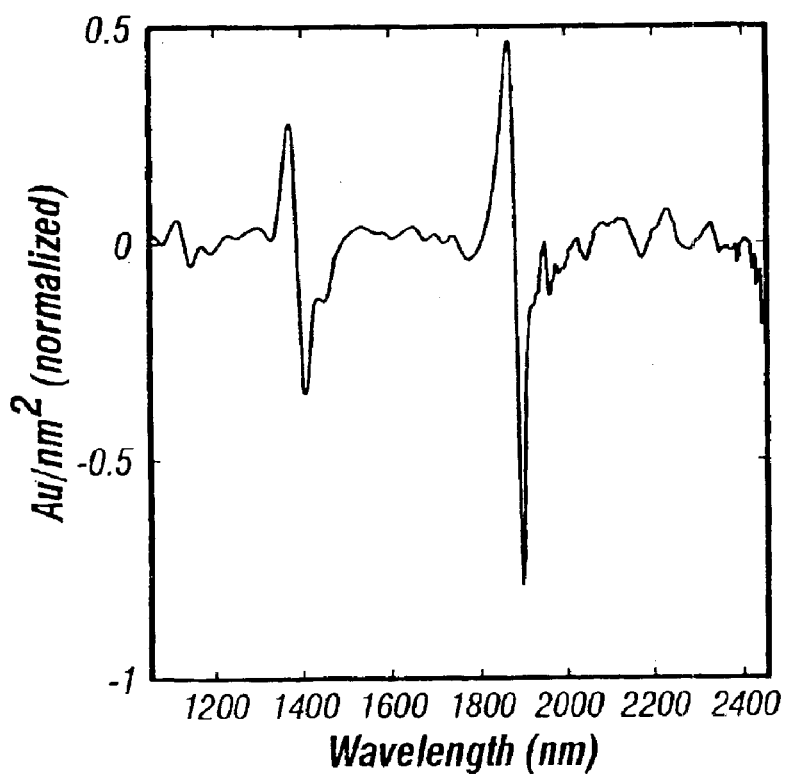
FIG. 4 shows a normalized second derivative of an absorbance spectrum versus wavelength.
Figure 5:
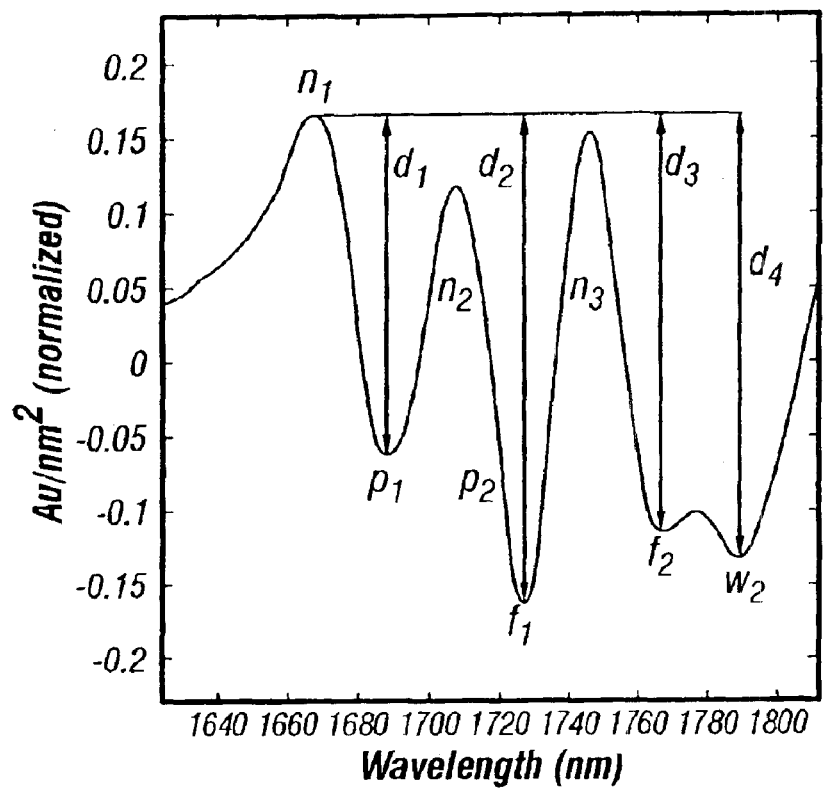
FIG. 5 shows the second derivative of an absorbance spectrum in the first overtone with features identified according to the invention.
Figure 6:
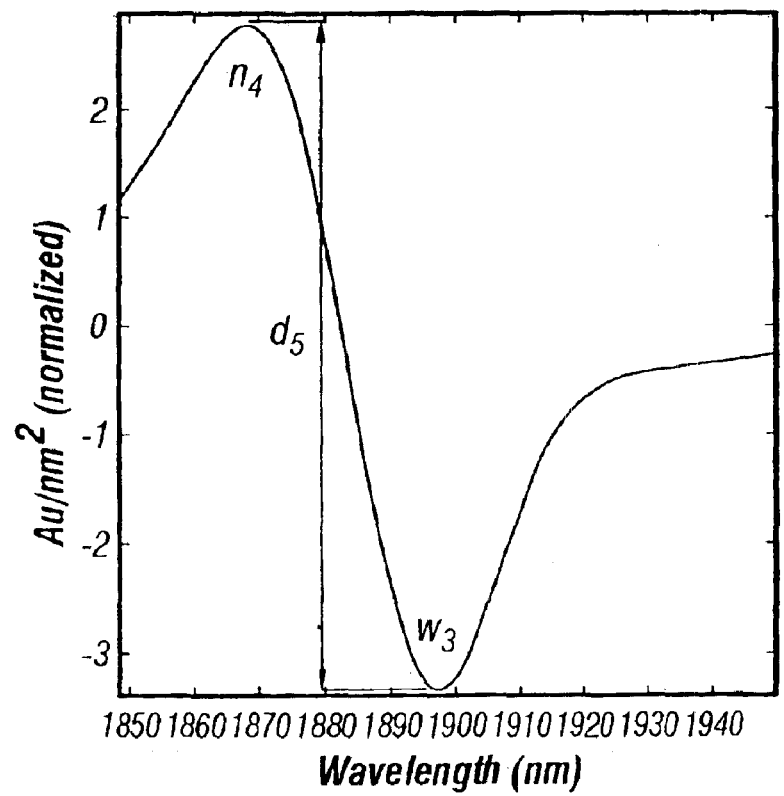
FIG. 6 shows the second derivative of the absorbance spectrum of FIG. 5 in the vicinity of the 1910 nm water band.
Figure 7:
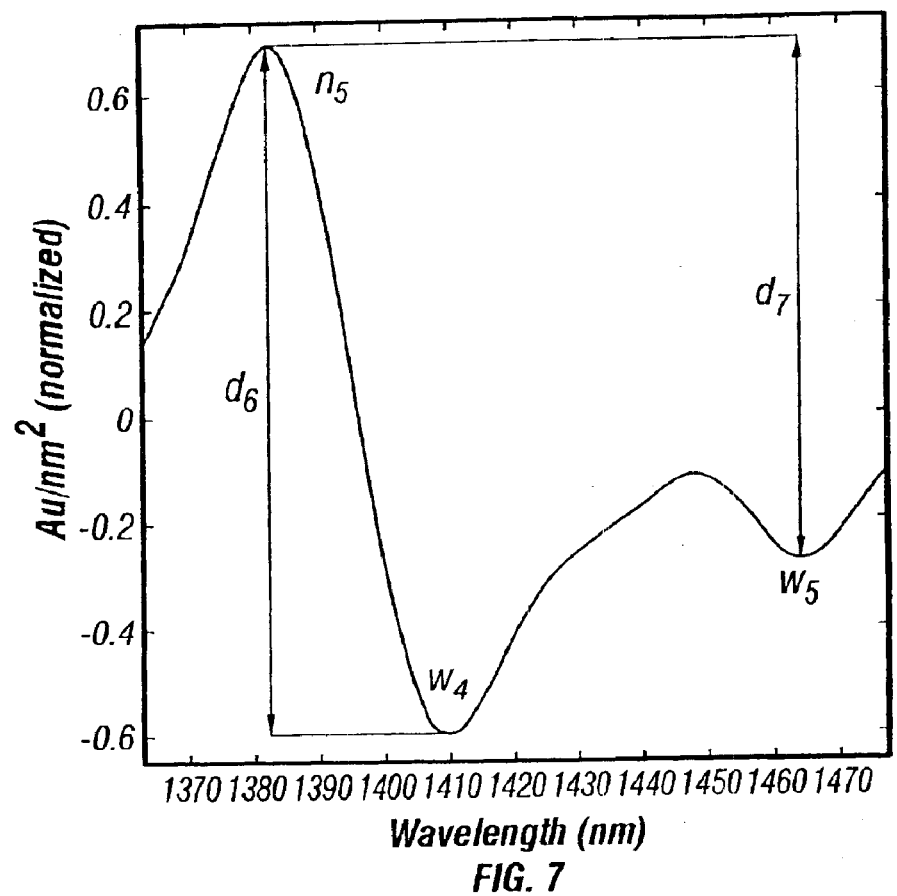
FIG. 7 shows the second derivative of the absorbance spectrum of FIG. 4 in the vicinity of the 1450 nm water band.
Figure 8:
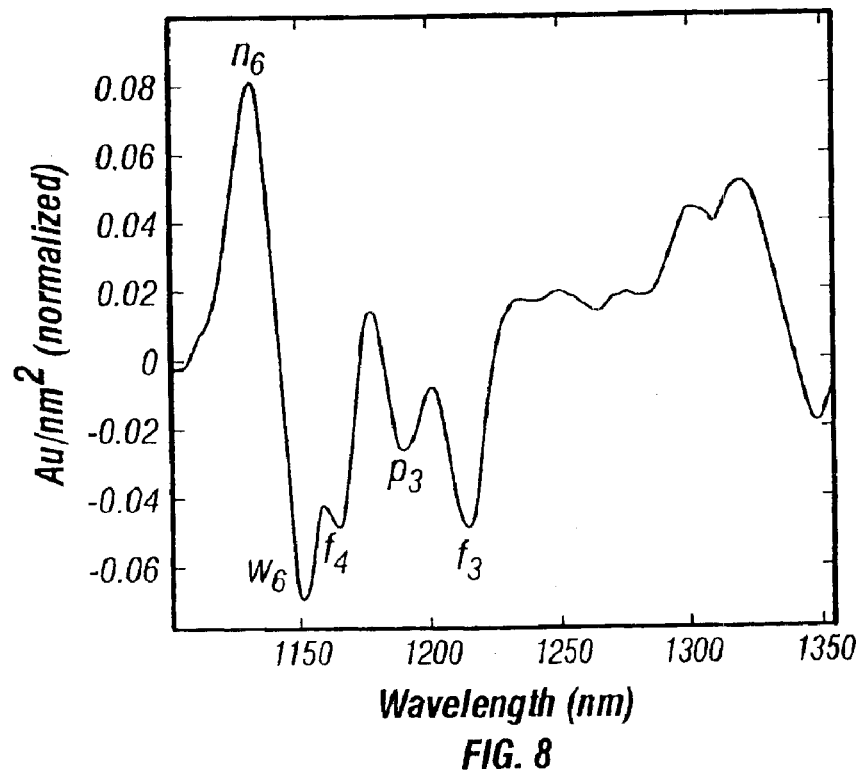
FIG. 8 shows the second derivative of the absorbance spectrum of FIG. 5 in the second overtone region with exemplar features according to the invention.
Figure 9:
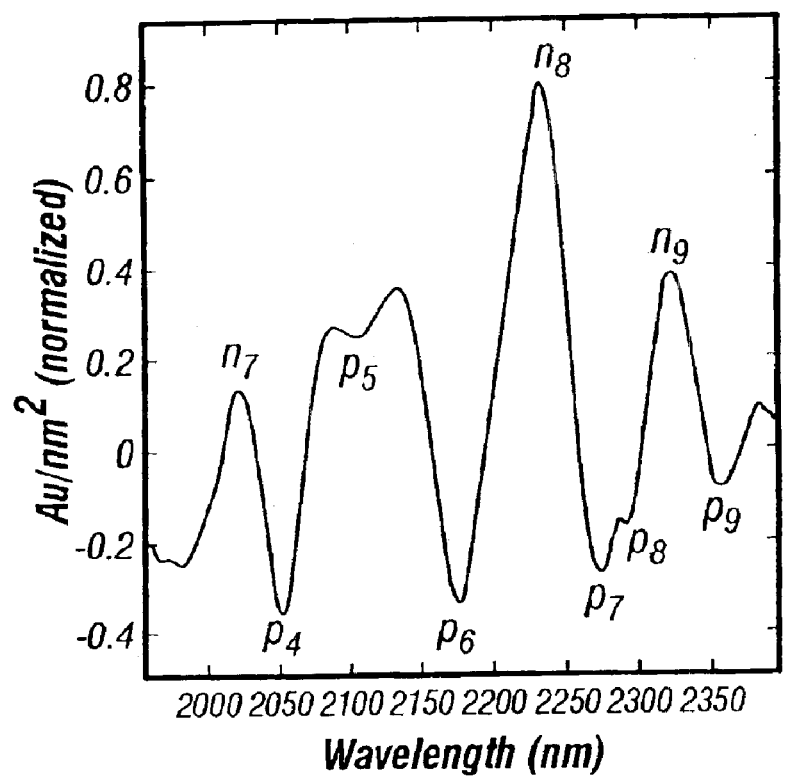
FIG. 9 shows the second derivative of the absorbance spectrum of FIG. 5 in the combination band with key features marked according to the invention.

In the preferred embodiment, the features are determined from the second derivative of the absorbance spectrum shown in FIG. 4. Each critical point is identified according to its wavelength. The value of the second derivative spectrum at each critical point is used as a feature to represent a key property of the tissue sample associated with the measurement spectrum. In FIGS. 5 through 9, many key features are identified as exemplary measurements. These include:

Normalization points (n) 1–8 near 1665, 1708, 1746, 1868, 1380, 1133, 2020 and 2232 nm respectively;

Fat bands points (f) 1–4 near 1727, 1765, 1214, 1165 nm;

Protein band points (p) 1–9 near 1687, 1715, 1190, 2050, 2150, 2175, 2275, 2292, and 2355 nm; and Water band points (w) 2–6 near 1789, 1896, 1410, 1465 and 1150 nm.

Normalization points, n1–n8, are generally used to determine derived features and points designated as "fat" (f1–f4), "protein" p1–p9 and "water" w2–w6 are generally located in the vicinity of an absorption band due to fat, protein or water respectively. Due to the bandwidth (lower resolution) of the second derivative spectrum, several of the bands associated with one constituent include absorbance due to another and a few of the critical points are associated with a constituent because their location is in the vicinity of the respective constituent. In addition, the wavelengths are reported for the features shown in the example second derivative spectrum and can change substantially as a result of variation in the reduced scattering coefficient and the inner filter effect related to the multiple layers of the skin.

Additional features have been derived and are noted on the plots. For example, $d1=n_{1665}-P_{1687}$, $d2=n_{1665}-f_{1727}$, $d3=n_{1665}-f_{1765}$, $d4=n_{1665}-w_{1789}$, $d5=n_{1868}-w_{1410}$, $d6=n_{1380}-w_{1465}$ and $d7=n_{1380}-w_{1150}$, where the notation $p_\lambda$, $w_\lambda$, $f_\lambda$, and $n_\lambda$ designate the protein, water, fat or normalization points designated previously that are close to the wavelength $\lambda$. Additional derived features that are used for outlier detection and measurement include d2/d1.

While specific examples of features have been provided in this context, one skilled in the art will recognize that many useful features have not been listed that can be derived from the absorbance spectrum, the first derivative spectrum or a preprocessed absorbance spectrum. Additionally, a principal components analysis provides additional abstract features that are useful for tissue transient identification, outlier analysis and analyte measurement. In certain instances, the entire spectrum, after suitable preprocessing, is passed to the measurement module in which a calibration is applied to estimate or predict the concentration of blood glucose.

Finally, features related to the absorption of glucose are extracted through preprocessing, wavelength selection and abstract feature selection. In the preferred embodiment preprocessing includes on or more steps of filtering, differentiation, scatter correction and normalization. Wavelength selection limits the spectrum to regions pertaining specifically to glucose including 1450–1700 nm, 1700–1900 nm, 2050–2200 nm, and 2250–2400 nm.

Tissue Template (102)

A background subtraction step follows the preprocessing steps defined above through the determination of the difference between the estimated spectral background or tissue template 102 and x through $$z = x - (cx_t + d) \tag{5}$$

where x is the preprocessed spectrum or the selected set of features, $x_t$ is the estimated background or tissue template associated with the measurement period, and c and d are slope and intercept adjustments to the tissue template. During each measurement period, defined by a measurement position on the tissue and a level of physiological stability of the measurement site, the tissue template is determined through one or more spectral measurements and a data selection criterion, for example, by selecting only spectral measurements that resemble each other closely and averaging them. In the preferred embodiment, $x_t$ includes features extracted from a (spectral) measurement collected on tissue at the beginning of the measurement period. This process is referred to as "re-calibration" and involves both the collection of one or more spectral measurements that are processed to form a tissue template as well as an associated set of reference glucose values. The glucose values are combined, according to the same strategy as that used to create the tissue template to form a measurement bias adjustment 103, described in greater detail below. The measurement period is defined as a time period during which the state of the tissue sample is uniform (optical properties within a preset bound) and the tissue measurement site is constant. However, the tissue template can also be any set of features from a given patient or calibration set that future spectral measurements will be compared with. In this latter embodiment, the variables c and d are determined through a least-squares fit (to minimize the Euclidean norm of z) of the tissue template over a particular wavelength range to the measured spectrum.

Detection of Tissue States

As discussed previously, changes in the distribution of water in the various compartments lead to changes in the optical properties that are reflected by changes in the spectral features. Therefore, conditions that are detrimental to spectroscopic glucose measurement can be detected by monitoring the selected features and ensuring that their variation over a given measurement period does not exceed that of the calibration set or some other previously established limit. For example, the variation of d2 ($n_{1665}-f_{1727}$), the magnitude of the normalized fat band, has been used to determine hydration state of the dermis. If the magnitude of d2, compared to the tissue template, exceeds the total variation or the range established by samples selected to calculate the calibration model, an error is indicated. Similarly, the normalized protein band (d1=$n_{1665}-p_{1687}$), various normalized water bands (d4=$n_{1665}-w_{1789}$, d5=$n_{1858}-w_{1410}$, d6=$n_{1380}-w_{1465}$ and d7=$n_{1380}-w_{1150}$) and the ratio d1/d2 are used to detect outliers 107 and conditions that are not conducive to glucose measurement. This method can be applied to any of the identified features listed previously.

Measurement (109)

The measurement of glucose is accomplished through the application of a calibration model 108 to the processed spectral measurement and/or the extracted features. The model is determined from a calibration set of exemplary paired data points each consisting of a pre-processed spectral measurement (x) and an associated reference glucose value (y) determined from an analysis of a sample of blood or interstitial fluid. Alternately, the reference glucose measurements can be determined from a blood draw at the fingertip or site of the spectral measurement. Finally, the reference glucose measurements can be determined from interstitial glucose concentrations taken at or near the site of spectroscopic measurement or alternate representative site, for example the forearm.

According to this process, blood, serum, plasma or interstitial draws are taken from a tissue site that is either near the sensor sample site or has been designed/determined to reflect the sample site. For example, when non-invasive near-infrared measurements are taken for calibration on the forearm, it is possible in some individuals to collect a capillary blood draw from the same forearm or the opposite forearm. Alternately, rather than using blood draws, it is beneficial in some instances to use interstitial glucose values rather than capillary glucose values.

The calibration set is based on one or more subjects and generally contains glucose concentrations that span the expected range of glucose variation and that include spectral variation representative of that likely to be encountered in future spectral measurements. The calibration model 108 includes an equation, a set of parameters and corresponding computer code that is implemented to measure the subject's glucose level on the basis of the preprocessed spectral measurement. In the preferred embodiment, the preprocessing and feature extraction, together with the model, efficiently extract the net analyte signal of glucose where net analyte signal is the portion of the spectral signal related to the target analyte that is orthogonal to the interference [A. Lorber, K. Faber, B. Kowalski, *Net Analyte Signal Calculation in Multivariate Calibration*, Anal. Chem, 69, pp. 1620–1626 (1997)]. The net analyte signal is then scaled and bias corrected 103 to match the desired units of glucose measurement (e.g. mg/dL).

Several embodiments of the invention are disclosed under two categories. In the first measurement category the extracted features are supplemental and are applied to compensate another model for variation in the optical properties related to a change in the effective pathlength of detected light and sample tissue volume but which changes are unrelated to absorption due to glucose. This is accomplished by using the absorption features that reflect the changes in tissue optical properties related to a water shift between compartments (or other physiological transient condition) to supplement a calibration that is based on the near-infrared absorption of glucose.

In the second measurement category, the extracted features related to the physiological and chemical response of the body are primary and used to indirectly measure the subject's glucose level. The method is based on the natural response to changes in blood glucose, which result in the alteration of fluid distribution in the interstitial, vascular and cellular compartments. Such alteration of fluid distribution causes changes in the scattering and absorption properties of tissue that are detectable through near-infrared spectroscopy and which serve as a basis for an indirect blood glucose measurement. The near-infrared signal reflects the changes in the scattering properties from different layers in skin that coincide with changes in glucose concentration. Thus, the changes in fluid distribution lead to changes in the apparent absorption of key constituents, such as fat, protein and water that provide a signal that is substantially higher than that of glucose and can be used as markers for measuring glucose noninvasively. However, long-term fluid compartment balances are influenced by fluid intake, exercise, diet, drug therapy and other physiological factors.

The "ancillary" calibration of glucose to fluid compartment shifts is possible over short term periods while the calibration of glucose to fluid shifts over longer periods of time requires a bias correction of the analytical signal and the associated blood glucose to compensate for the sources of long term fluid compartment shifts (it is noted that Fick's Law in Equation 2 relates the flux in water concentration to the change in glucose concentration). Thus, this measurement only permits the determination of the movement of glucose relative to an initial point in time; and bias correction of both the spectroscopic water signal and the associated glucose concentration to this point is required because the initial water concentration is not strictly a function of the associated glucose concentration. Therefore, in this embodiment of the invention, there is provided an apparatus and method that measures the change in the optical properties of tissue as reflected in key constituents and a method for determining the glucose concentration on the basis of these properties.

Supplemental measurement of glucose through spectral features is performed either through the classification system previously disclosed or by supplementing the glucose measurement model with the selected features through the general equation:

$$\hat{y}=f(x_p,z)+b \tag{1}$$

where $\hat{y}$ is the estimated glucose concentration, $x_p \in \Re^N$ is a processed spectral measurement, $z \in \Re^M$ is the set of features representative of the physiological state or optical properties of the tissue, $f:\Re^{N,M} \to \Re^1$ is a model used to measure glucose on the basis of the preprocessed spectrum and extracted features, and b is a baseline adjustment for the glucose measurement associated with both the tissue template and calibration model. The model, $f(\cdot)$, is determined through a calibration set including spectral measurements, extracted features and reference glucose values (from blood or interstitial measurements). The method for designing the structure of $f(\cdot)$ is through the process of system of identification [L. Ljung, *Systems Identification: Theory for the User*, 2d.ed., Prentice Hall (1999)]. The model parameters are calculated using known methods including multivariate regression or weighted multivariate regression [N. Draper, H. Smith, *Applied Regression Analysis*, 2d.ed., John Wiley and Sons, New York (1981)], principal component regression [H. Martens, T. Naes, *Multivariate Calibration*, John Wiley and Sons, New York (1989)], partial least squares regression [P. Geladi, B. Kowalski, Partial least-squares regression: a tutorial, Analytica Chimica Acta, 185, pp. 1–17, (1986)], or artificial neural networks [S. Haykin, *Neural Networks: A Comprehensive Foundation*, Prentice Hall, Upper Saddle River N.J. (1994)].

In the case in which $x_p$ and z are independent, the general equation can be reduced to:

$$\hat{y}=f(x_p)-(m_s g(z)+m_i)+b \tag{2}$$

where $f:\Re^N \to \Re^1$ is a model used to measure glucose in the absence of physiological or other tissue variation, $g:\Re^M \to \Re^1$ is a model used to map the features to a variable correlated to the error in glucose measurement caused by a change in the optical properties of the tissue, and $m_s$ and $m_i$ are slope and intercepts used to convert g(z) to the correct units. In this case, it is possible to determine $f(\cdot)$ and $g(\cdot)$ separately through an experimental design. First, $f(\cdot)$ is found through an experiment in which the tissue optical properties are stable or constant while the glucose is manipulated. Second, the optical properties of tissue are allowed to fluctuate and $g(\cdot)$, $m_s$ and $m_i$ are determined on the basis of the error in glucose measurement where the target value for $g(\cdot)$ is given by:

$$r=y-f(x_p)-b \tag{3}$$

where y is the reference glucose concentration. In the third embodiment, when $f(\cdot)$ and $g(\cdot)$ are determined to be linear over the range of measurement, equation #8 reduces to:

$$\hat{y}=x_p F-(m_s zG+m_i)+b \tag{4}$$

where $F \in \Re^{N \times 1}$ and $G \in \Re^{M \times 1}$. In this embodiment, F and G are determined separately as described above using linear methods of calibration. This final realization of the supplemental use of features for glucose measurement is the preferred method.

In the second category of measurement the extracted features are used to indirectly measure glucose through:

$$\hat{y}=(m_s g(z))+b \tag{5}$$

where $g:\Re^M \to \Re^1$ is a model used to map the features to a variable correlated to the reference glucose level and $m_s$ and $m_i$ are slope and intercepts used to convert g(z) to the correct units. The method for determining $g(\cdot)$ is through an exemplary set (calibration set) of spectral measurements, extracted features and reference glucose concentrations (from blood or interstitial measurements). A sub-set of features is selected based on their combined correlation to the reference glucose concentration. While a priori knowledge and trial-and-error can be employed for variable selection, standard methods also exist for variable selection including stepwise regression [Draper, et al., supra] random search techniques, genetic algorithms [D. Goldberg, *Genetic Algorithm in Search, Optimization and Machine Learning*, Addison Wesley Publishing Company (1989)] or evolutionary programming [D. Fogel, *An Introduction to Simulated Evolutionay Optimization*, IEEE Trans. On Neural Networks, 5:1 (January 1994)]. The model, $g(\cdot)$, is determined through standard methods of linear or nonlinear calibration. In the linear case, $$\hat{y}=(m_s zG+m_i)+b, \tag{6}$$

where $G \in \Re^{M \times 1}$.

Figure 10:
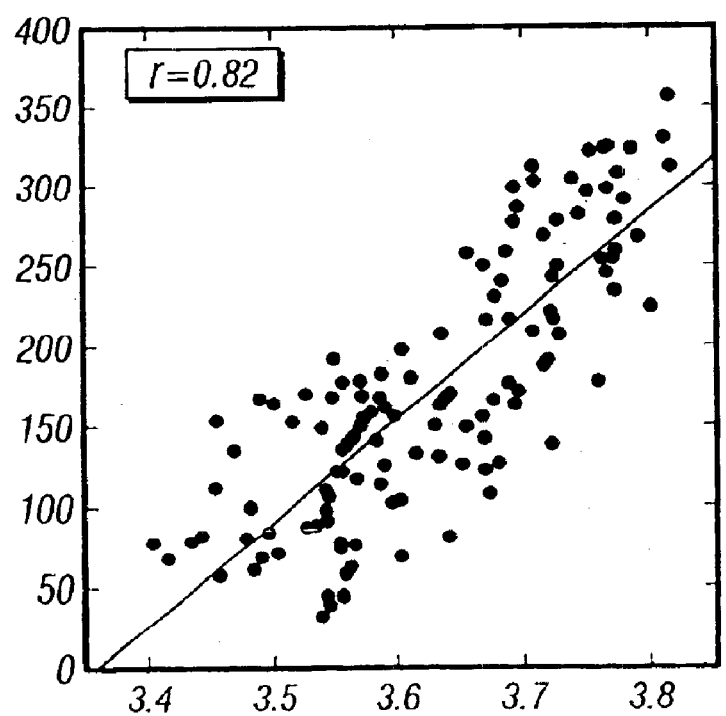
FIG. 10 shows a plot of a normalized fat band versus glucose concentration according to the invention.

In the preferred embodiment of the invention, the features, z, are selected to include at least the normalized second derivative fat band (d2) or the normalized second derivative protein band (d1). The parameters of the model ($m_s$, $m_i$ and G) are determined through multivariate regression, weighted multivariate regression or locally weighted regression. For example, a calibration set was collected on a particular subject whose glucose concentration spanned the range 70–350 mg/dl. A plot of the normalized fat band, d2, versus glucose concentration is given in FIG. 10. The high degree of correlation between the feature and reference glucose concentration indicates that glucose measurement is feasible through this extracted feature. A simple linear regression is performed to determine the model parameters of the equation above.

However, the invention is not limited to the normalized fat and protein bands. A similar method has been developed using the water absorbance peaks and normalized water absorbance peaks ($d4=n_{1665}-w_{1789}$, $d5=n_{1868}-w_{1410}$, $d6=n_{1380}-w_{1466}$ and $d7=n_{1380}-w_{1150}$). Also the wavelength chosen for normalization is not restricted to 1665 nm. In fact, a multiplicity of models exists for various subjects and categories of subjects depending on the optical properties of their respective tissue sample, baseline level of perfusion and physiological response to changes in glucose concentration. Thus, an alternative embodiment consists of using a combination of features related to all of the major types of absorption bands. For example, the normalized second derivative fat band and two normalized second derivative water bands were selected. Multiple regression of these variables against glucose was then performed using a model which could be but not restricted to, $$\hat{y}=g_1 z_1+g_2 z_2+g_3 z_3+g_4+b \tag{12}$$

where $z_1$, $z_2$ and $z_3$ are the normalized second derivative values of the fat band and two water bands respectively. This equation can then be used to measure glucose values from spectra taken in the future after preprocessing and feature extraction.

In an alternate embodiment, abstract features that reflect the changes in the optical properties of skin tissue, such as the scores from a principal components analysis, can be used as the independent variables for noninvasive calibration and measurement of glucose. In this embodiment, the spectral measurement, m, is preprocessed and is followed by wavelength selection to create the preprocessed vector, x. A spectral decomposition is performed according to $$z = xP \quad (13)$$

where $x \in \Re^{1 \times N}$ is the preprocessed spectrum, N refers to the number of wavelengths selected for calibration, $P \in \Re^{1 \times M}$ is the set of M eigenvectors or loadings obtained from a principal components analysis of the calibration set, and $z \in \Re^{1 \times M}$ is the set of abstract features or scores used to develop a calibration model and measure glucose through Equation (14) below, or through the application of a non-linear calibration model. As described above, the calibration model can be determined through multivariate regression, weighted multivariate regression, locally weighted regression or other standard approach. While principal component regression has been described as the method for spectral decomposition, partial least squares regression can also be applied.

When abstract feature extraction is involved, the preferred method involves preprocessing through a first derivative with a wide smoothing window (e.g., 31 nm), scatter correction through multiplicative scatter correction or standard normal variate transformation [R. Barnes, M. Dhanoa, S. Lister, Applied Spectroscopy, 43:772–777 (1989], and wavelength selection in the range 1450–1850 nm or a subset thereof. In addition, information from a water band, such as 1180–1450 nm may also be included. The preprocessed data is corrected to the tissue template and partial-least squares is applied to develop the calibration model. Glucose is then measured through the application of the identical preprocessing steps to a spectral measurement (first derivative, scatter correction, wavelength selection and tissue template correction) to obtain the processed spectral measurement, x. The glucose measurement associated with the spectral measurement is determined according to $$\hat{y} = xG + b \quad (13)$$

where $G \in \Re^{M \times 1}$ is a linear transformation, derived from partial least-squares regression that represents both the feature extraction step and the calibration model.

While the invention has been described herein with respect to measurement of glucose in blood and tissue, the principles of the invention find application in detection of other tissue constituents and analytes as well.

Although the invention has been described herein with reference to certain preferred embodiments, one skilled in the art will readily appreciate that other applications may be substituted for those set forth herein without departing from the spirit and scope of the present invention. Accordingly, the invention should only be limited by the claims included below.

What is claimed is:

1. A method for noninvasive measurement of a target analyte in a tissue sample, comprising the steps of:
   measuring a spectrum of a tissue sample;
   detecting at least one optical property of said tissue sample related to fluid shift between extravascular and intravascular tissue compartments triggered by changes in concentration of said analyte, as manifested by at least one spectral feature reflecting said fluid shift; and
   either correcting a direct analyte measurement on the basis of said at least one optical property; or
   measuring said analyte indirectly on the basis of said at least one optical property.

2. The method of claim 1, wherein said step of measuring a spectrum comprises measuring a spectrum, m, of said tissue, said spectrum denoted by a vector $m \in \Re^{1 \times N}$ of absorbance values pertaining to a set of N wavelengths, $\lambda \in \Re^N$ spanning near IR region of approximately 700 to 2500 nm.

3. The method of claim 2, wherein m comprises a set of wavelengths in the near IR that have been optimized for extraction of features.

4. The method of claim 1, further comprising the step of preprocessing said spectrum, preprocessing comprising any of:
   filtering;
   calculating a first or second derivative of said spectrum; and scatter correction.

5. The method of claim 1, further comprising the step of extracting said at least one features, feature extraction comprising any mathematical transformation that enhances a quality or aspect of a sample measurement for interpretation so that structural properties and physiological state of said tissue sample are concisely represented.

6. The method of claim 5, wherein said feature extraction step comprises the steps of:
   identifying distinct absorption bands that change in differing manners with respect to changes in pathlength, scattering and absorption properties of the sample;
   developing a set of features that represents or reflects the optical properties of the tissue; and
   applying said features to identify;
      conditions suitable for analyze measurement; and
      conditions unsuitable for analyte measurement.

7. The method of claim 5, wherein features include any of:
   at least one simple features, comprising values of a spectral measurement or a processed spectral measurement at critical points, wherein a critical point is a point having a slope of zero;
   a derived features, comprising at least one features derived from simple features through a mathematical transformation; and
   an abstract features;
   wherein simple and derived features generally have a physical interpretation, and wherein abstract features do not necessarily have a specific interpretation related to a physical system.

8. The method of claim 7, wherein an abstract features comprises scores from a principal component analysis, wherein leading principal components represent variation related to the structural properties and physiological state of the tissue sample, so that the optical properties of the tissue are represented.

9. The method of claim 7, wherein a feature is determined from a second derivative of said spectrum, wherein value of said second derivative spectrum at each critical point constitutes a feature that represents a key property of the sample.

10. The method of claim 9, wherein a feature includes any of:
   a normalization point;
   a fat band point;

a protein band point; and a water band point;

wherein a normalization point is used to determine a derived feature, and fat, protein, and water points are respectively located in vicinity of an absorption band due to fat, protein, or water.

11. The method of claim 1, further comprising the step of:

determining difference between a tissue template and a preprocessed spectrum according to:

$$z=x-(cx_t+d);$$

wherein x comprises a pre-processed spectrum or a selected set of features, $x_t$ comprises a tissue template associated with a measurement period, and c and d are slope and intercept adjustments to the tissue template.

12. The method of claim 11, wherein said tissue template is determined through one or more spectral measurements combined according to a predetermined data selection criterion during each measurement period.

13. The method of claim 12, wherein a measurement period comprises a time period during which the state of the tissue sample is uniform and measurement site is constant.

14. The method of claim 12, further comprising the step of:

providing an associated set of reference analyte values, said values combined according to said predetermined data selection criterion to form a measurement bias adjustment.

15. The method of claim 11, wherein said tissue template comprises any set of features from a given subject or calibration set that future spectral measurements will be compared with, wherein c and d are determined are determined through least-squares fit of the tissue template over a particular wavelength range to the measured spectrum.

16. The method of claim 1, further comprising any of the steps of:

detecting conditions not conducive to analyte measurement; and detecting outliers.

17. The method of claim 16, said step of detecting conditions not conducive to analyte measurement comprising the steps of:

monitoring at least one selected features; and ensuring that variation in said at least one selected feature over a given measurement does not exceed that of a calibration set or another previously established limit.

18. The method of claim 1, further comprising the step of providing a calibration model, said model determined from a calibration set of exemplary paired data points each consisting of a preprocessed spectral measurement, x and an associated reference analyte value, y, said calibration set including analyte concentrations that span the expected range of variation and spectral variation representative of future spectral measurements, said model comprising an equation, a set of parameters and corresponding computer code implemented to measure a subject's analyte level on the basis of a processed spectral measurement.

19. The method of claim 18, wherein said y values are determined from samples of blood, serum, plasma or interstitial fluid taken from a fingertip, a site near the measurement site or an alternate site.

20. The method of claim 19, wherein said alternate site comprises a sample site that has been designed or determined to reflect the sample site.

21. The method of claim 18, wherein said parameters are calculated using any of:

multivariate regression:

weighted multivariate regression:

principal component regression;

partial least squares regression; and artificial neural networks.

22. The method of claim 18, wherein said step of correcting a direct analyte measurement on the basis of said detected changes comprises supplementing said model with selected features according to:

$$\hat{y}=f(x_p,z)+b,$$

where $\hat{y}$ is an estimated glucose concentration, $x_p \in \Re^N$ is a processed spectral measurement, $z \in \Re^M$ is a set of features representative of the physiological state or optical properties of the tissue, $f:\Re^{N,M} \to \Re^1$ is a model used to measure glucose on the basis of a preprocessed spectrum and at least one extracted features, and b is a baseline adjustment for glucose measurement associated with both a tissue template and said calibration model.

23. The method of claim 18, wherein said step of correcting a direct analyte measurement on the basis of said detected changes comprises supplementing said model with selected features according to:

$$\hat{y}=f(x_p)-(m_s g(z)+m_i)+b,$$

where $\hat{y}$ is an estimated glucose concentration, $x_p \in \Re^N$ is a processed spectral measurement, $z \in \Re^M$ is a set of features representative of the physiological state or optical properties of the tissue, wherein $x_p$ and z are independent, where $f:\Re^N \to \Re^1$ is a model used to measure glucose in the absence of physiological or other tissue variation, $g:\Re^M \to \Re^1$ is a model used to map the features to a variable correlated to error in glucose measurement caused by a change in the optical properties of the tissue, $m_s$ and $m_i$ are slope and intercepts used to convert g(z) to correct units, and b is a baseline adjustment for glucose measurement associated with both a tissue template and said calibration model.

24. The method of claim 23, wherein f(·) and g(·) are separately determined experimentally, wherein f(·) is determined by manipulating glucose while tissue optical properties remain constant, and wherein the optical properties of tissue are allowed to fluctuate and g(·), $m_s$ and $m_i$ are determined on the basis of the error in glucose measurement where target value for g(·) is given by:

$$r=y-f(x_p)-b$$

where y is a reference glucose concentration.

25. The method of claim 24, wherein said step of correcting a direct analyte measurement on the basis of said detected changes comprises supplementing said model with selected features according to:

$$\hat{y}=x_p F-(m_s zG+m_i)+b,$$

wherein f(·) and g(·) are determined to be linear over range of measurement and where:

$F \in \Re^{N \times 1}$ and $G \in \Re^{M \times 1}$.

26. The method of claim 18, wherein said step of measuring said analyte indirectly on the basis of said at least one spectral features comprises using extracted features to measure glucose indirectly according to:

$$\hat{y}=(m_s g(z)+m_i)+b$$

where $g:\Re^M \to \Re^1$ comprises said model, said model used to map set of features z to a variable correlated to a reference glucose level concentration and $m_s$ and $m_i$ are slope and intercepts used to convert g(z) to the correct units and b is a baseline adjustment for glucose measurement.

27. The method of claim 26, wherein said at least one feature is selected based an their combined correlation to the reference glucose concentration.

28. The method of claim 27, wherein said at least one features is selected based on any of:
   a priori knowledge;
   trial-and-error;
   stepwise regression;
   random search techniques;
   genetic algorithms; and
   evolutionary programming.

29. The method of claim 2, wherein g(·) is determined according to:

$$\hat{y}=(m_s zG+m_i)+b,$$
where $G \in \Re^{M \times 1}$.

30. The method of claim 26, wherein z includes either a normalized second derivative fat b and or protein band, and wherein $m_s$, $m_i$ and G are determined through any of multivariate regression, weighted multivariate regression and locally weighted regression.

31. The method of claim 26, wherein said step of measuring said analyte indirectly on the basis of said at least one spectral features comprises using an extracted feature to measure glucose indirectly according to:

$$\hat{y}=g_1 z_1+g_2 z_2+g_3 z_3+g_4+b,$$

where $z_1$, $z_2$ and $z_3$ comprise normalized second derivative values of a fat band and two water bands, respectively.

32. The method of claim 1, wherein said step of measuring said analyte indirectly comprises:
   providing a noninvasive glucose calibration model wherein abstract features that reflect said changes in optical properties of said tissue are used as independent variables for said calibration;
   preprocessing said measured spectrum; and
   decomposing said preprocessed spectrum according to:

$$z=xP$$

where $x \in \Re^{1 \times N}$ is the preprocessed spectrum, N is number of wavelengths selected for calibration, $P \in \Re^{1 \times M}$ is a set of M eigenvectors or loadings obtained from a principal components analysis of a calibration set and $z \in \Re^{1 \times M}$ is the set of abstract features used to measure glucose through application of said calibration model, wherein said model is either linear or nonlinear.

33. The method of claim 32, wherein said abstract feature comprises scores from a principal component analysis.

34. The method of claim 32, wherein providing said calibration model comprises the steps of:
   preprocessing spectral measurements from said calibration set through a first derivative with a wide smoothing window;
   scatter correcting said preprocessed measurements from said calibration set through multiplicative scatter correction or standard normal variate transformation;
   selecting wavelengths from a range of approximately 1450–1850 nm and optionally 1180–1450 nm;
   correcting said preprocessed, scatter-corrected data to a tissue template: and
   applying partial least squares regression.

35. The method of claim 34, further comprising the steps of:
   applying identical processing to said measured spectrum as applied in developing said calibration model.

36. The method of claim 35, further comprising the step of:
   determining a glucose measurement according to:

$$\hat{y}=mG+b$$

where $G \in \Re^{M \times 1}$ is the calibration model derived from partial least-squares regression and b is a baseline correction.

37. The method of claim 1, wherein said analyte comprises glucose.

38. An apparatus for noninvasive measurement of a target analyte in a tissue sample comprising:
   means for measuring a spectrum of a tissue sample:
   means for detecting at least one optical property of said tissue sample related to fluid shift between extravascular and intravascular tissue compartments triggered by change in concentration of said analyte, as manifested by at least one spectral features reflecting said fluid shifts; and
   either correcting a direct analyte measurement on the basis of said at least one optical property; or
   measuring said analyte indirectly on the basis of said at least one optical property.

39. The apparatus of claim 38, wherein said means for measuring a spectrum of a tissue sample comprises a spectrometer system, said spectrometer system comprising:
   a source of near infrared (NIR) radiation;
   a wavelength selection element;
   a means for interfacing with the measurement site on the skin of a subject, wherein radiation is directed toward the measurement site from the source, and a light signal returned from the site is collected;
   means for detecting said returned radiation; and
   means for digitizing said returned signal.

40. The apparatus of claim 39, wherein said NIR source radiates energy in a range of approximately 700–2500 nm.

41. The apparatus of claim 39, wherein said NIR source comprises any of:
   an LED array; and
   a halogen lamp.

42. The apparatus of claim 39, further comprising a band pass filter to minimize effect of wavelengths radiated from said source that are outside a spectral range of interest.

43. The apparatus of claim 39, wherein said wavelength selection element comprises any of:
   a dispersive element;
   an interferometer; and
   successive illumination of elements of an LED array.

44. The apparatus of claim 43, further comprising a reference wavelength standard, wherein changes in said wavelength selection element caused by environmental changes are compensated by scanning said standard proximate to or simultaneous with interrogation of said tissue.

45. The apparatus of claim 39, wherein said means for interfacing with the measurement site on the skin of a subject comprises:
   at least one optical element that directs radiation to and/or from the tissue, said optical element including any of:
   a light pipe:
   a fiber optic;
   a lens system: and
   a light directing mirror system.

46. The apparatus of claim 45, said means for interfacing with the measurement site on the skin of a subject further comprising:
a guide to assist in interfacing said optical element and said measurement site.

47. The apparatus of claim 46, said means for interfacing with the measurement site further comprising a subject interface module, said subject interface module including at least an elbow rest and a wrist rest.

48. The apparatus of claim 45, said means for interfacing with the measurement site on the skin of a subject further comprising:
an optical coupling fluid, a portion of said fluid being interposed between said measurement site and said source to minimize specular reflectance from surface of the skin.

49. The apparatus of claim 39, wherein an area irradiated and an area from which returning radiation is collected from are separated by a preselected distance, said distance selected to target a tissue volume conducive to measurement of a property of interest.

50. The apparatus of claim 39, wherein said means for detecting said returned radiation comprises:
a single diodes or a diode array responsive to targeted wavelengths of interest.

51. The apparatus of claim 50, wherein said diodes include InGaAs detectors.

52. The apparatus of claim 50, wherein said diodes are selected such that material junctions in said diodes do not coincide with targeted wavelengths.

53. The apparatus of claim 50, wherein said diodes convert said signal to a voltage.

54. The apparatus of claim 39, said means for digitizing said returned signal comprises an ADC (analog-to-digital converter), wherein said signal, having been converted to a voltage, is digitally sampled for analysis on a microprocessor-based system.

55. The apparatus of claim 54, further comprising a display, wherein a result of said analysis is displayed.

56. The apparatus of claim 38, wherein said means for detecting at least one optical property of said tissue sample related to fluid shift in said tissue, as manifested by said at least one spectral feature reflecting said changes; and
either correcting a direct analyte measurement on the basis of said at least one spectral feature; or
measuring said analyte indirectly on the basis of said at least one spectral feature comprises an analyzer, said analyzer including:
means for measuring a spectrum, m of said tissue, said spectrum denoted by a vector $m \in \Re^{1 \times N}$ of absorbance values pertaining to a set of N wavelengths, $\lambda \in \Re^{N}$ spanning near-infrared region of approximately 700 to 2500 nm.

57. The apparatus of claim 56, said analyzer further comprising:
means for preprocessing said spectrum.

58. The apparatus of claim 57, said analyzer further comprising:
means for extracting said at least one feature, comprising any mathematical transformation that enhances a quality or aspect of a sample measurement for interpretation so that structural properties and physiological state of said tissue sample are concisely represented.

59. The apparatus of claim 58, said analyzer further comprising:
a tissue template determined through one or more spectral measurements combined according to a predetermined data selection criterion during each a measurement period, said tissue template subtracted from said spectrum.

60. The apparatus of claim 59, said analyzer further comprising means for calculating a measurement bias adjustment.

61. The apparatus of claim 60, said analyzer further comprising
means for detecting outliers and conditions detrimental to spectroscopic glucose measurement though said at least one feature.

62. The apparatus of claim 61, said analyzer further comprising:
at least one calibration model, said model determined from a calibration set of exemplary paired data points each consisting of a spectral measurement, x and an associated reference analyte value, y, said calibration set including analyte concentrations that span the expected range of variation and spectral variation representative of future spectral measurements, said model comprising an equation, a set of parameters and corresponding computer code implemented to measure a subject's analyte level on the basis of a processed spectral measurement.

63. The apparatus of claim 38, wherein said analyte comprises glucose.

64. A method for noninvasive measurement of a target analyte property in a tissue sample, comprising the steps of:
noninvasively measuring a spectrum of a tissue sample in vivo;
detecting at least one optical property of said tissue sample related to physiologic state of said tissue resulting from change in concentration of said analyte, as manifested by at least one spectral feature reflecting said physiologic state; and
either correcting a direct analyte measurement on the basis of said at least one optical property; or
measuring said analyte indirectly on the basis of said at least one optical property.

65. A method for noninvasive measurement of glucose concentration in a tissue sample, comprising the steps of:
measuring a spectrum of a tissue sample;
detecting at least one optical property of said tissue sample related to state of said tissue resulting from change in concentration of glucose, as manifested by at lest one spectral feature reflecting said state; and
either correcting a direct glucose measurement on the basis of said at least one optical property; or
measuring said glucose concentration indirectly on the basis of said at least one optical property.

66. A method for noninvasive measurement of a target analyte in a tissue sample, comprising the steps of:
measuring a spectrum of a tissue sample;
detecting conditions not conducive to analyte measurement;
if conditions are conducive to analyte measurement, detecting at least one optical property of said tissue sample related to physiology of said tissue resulting from change in concentration of said analyte, as manifested by at least one spectral feature reflecting said physiology; and
either correcting a direct analyte measurement on the basis of said at least one spectral feature; or
measuring said analyte indirectly on the basis of said at least one optical property.

* * * * *